(12) United States Patent
Ladd et al.

(10) Patent No.: US 9,655,688 B2
(45) Date of Patent: May 23, 2017

(54) DENTAL INSTRUMENT

(71) Applicant: L & K Dental Instruments, Kokomo, IN (US)

(72) Inventors: John Ladd, Russiaville, IN (US); Joe Kinney, Kokomo, IN (US)

( * ) Notice: Subject to any disclaimer, the term of this patent is extended or adjusted under 35 U.S.C. 154(b) by 470 days.

(21) Appl. No.: 14/070,661

(22) Filed: Nov. 4, 2013

(65) Prior Publication Data
US 2015/0125816 A1 May 7, 2015

(51) Int. Cl.
*A61C 3/00* (2006.01)

(52) U.S. Cl.
CPC ..................... *A61C 3/00* (2013.01)

(58) Field of Classification Search
CPC .......... A61C 1/148; A61C 15/00; A61C 3/00; A61C 17/00; A61C 1/144
USPC ......................................................... 433/143
See application file for complete search history.

(56) References Cited

U.S. PATENT DOCUMENTS

| | | | | |
|---|---|---|---|---|
| 1,765,362 A * | 6/1930 | Berry | ...................... | B23B 31/20 279/145 |
| 3,479,041 A * | 11/1969 | Whipple | ................ | A61C 1/148 279/42 |
| 4,114,276 A | 9/1978 | Malata et al. | | |
| 4,743,198 A * | 5/1988 | Kennedy | .................. | A61C 3/00 433/143 |
| 4,759,713 A * | 7/1988 | Heiss | ....................... | A61C 3/00 433/141 |
| 4,820,154 A * | 4/1989 | Romhild | ................ | A61C 1/148 279/80 |
| 4,841,597 A | 6/1989 | Kolonia | | |
| 5,024,600 A * | 6/1991 | Kline | ................. | A61C 17/0202 433/143 |
| 5,030,091 A * | 7/1991 | Svanberg | ................. | A61C 3/00 433/141 |
| 5,328,370 A | 7/1994 | Chen | | |
| 5,383,785 A | 1/1995 | Brugger | | |
| 5,624,259 A * | 4/1997 | Heath | ....................... | A61C 3/00 433/141 |
| 6,099,310 A * | 8/2000 | Bornstein | ................ | A61C 3/00 15/236.05 |

(Continued)

*Primary Examiner* — Cris L Rodriguez
*Assistant Examiner* — Hao D Mai
(74) *Attorney, Agent, or Firm* — Woodard Emhardt Moriarty McNett & Henry LLP

(57) ABSTRACT

A dental instrument device includes a middle body with two ends, a pair of removable instrument tips, a pair of securing collets, and a pair of removable end caps. Each end of the middle body terminates in a middle body/instrument tip connection interface that receives a right-handed instrument tip only in a first orientation and a left-handed instrument tip only in a second orientation differing from the first orientation. The removable instrument tips have a similar middle body/instrument tip connection interface, and a working instrument end with a right-handed or a left-handed orientation. A right-handed instrument tip is releasably connected to the first middle body/instrument tip connection interface, and a left-handed instrument tip is releasably connected to the second middle body/instrument tip connection interface, with the right-handed and left-handed orientations being visually distinguishable one from the other by casual observation of an ordinary observer.

12 Claims, 17 Drawing Sheets

(56) References Cited

U.S. PATENT DOCUMENTS

| | | |
|---|---|---|
| 6,257,887 B1 | 7/2001 | Heckerman et al. |
| 6,293,792 B1 | 9/2001 | Hanson |
| 6,309,219 B1 * | 10/2001 | Robert .................... A61C 3/00 433/144 |
| 6,322,362 B1 | 11/2001 | Holms |
| 2002/0040198 A1 | 4/2002 | Rahman et al. |
| 2003/0093103 A1 | 5/2003 | Malackowski et al. |
| 2004/0115588 A1 | 6/2004 | Sommers et al. |
| 2005/0266377 A1 | 12/2005 | Tsao |
| 2006/0063123 A1 * | 3/2006 | Cleary .................... A61C 7/02 433/3 |
| 2006/0106363 A1 | 5/2006 | Aravena et al. |
| 2006/0131906 A1 | 6/2006 | Maurer et al. |
| 2007/0054239 A1 | 3/2007 | Maitre |
| 2011/0223559 A1 | 9/2011 | Jamnia et al. |
| 2012/0077148 A1 | 3/2012 | Luoto |
| 2015/0230880 A1 * | 8/2015 | Feine .................. A61C 1/0015 433/27 |

* cited by examiner

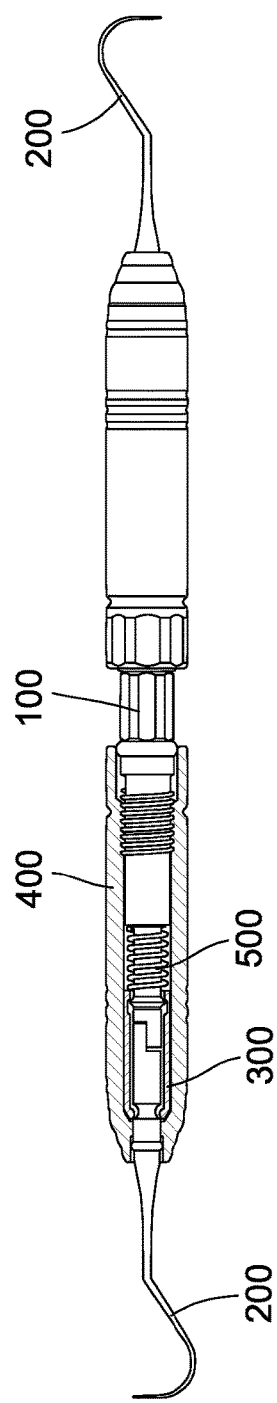
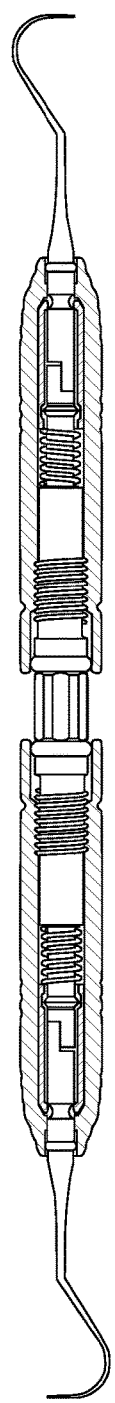
Fig. 1A
Fig. 1B

DENTAL INSTRUMENT

FIELD OF THE INVENTION

The present invention relates generally to dental instruments, and more particularly to a dental instrument having interchangeable tips.

BACKGROUND TO THE INVENTION

Dentists and dental hygienists frequently use hand tools to clean and repair teeth. For example, scalers and curettes are used to scrape away soft or small tartar deposits on teeth, while probes and explorers are used to determine the presence of decay on tooth enamel. Many of these tools have curved ends to facilitate reaching around and between teeth, and may be available in both right-handed and left-handed configurations to permit use in all areas of a patient's mouth.

The tips of dental tools must be sharpened periodically to maintain optimum performance. Moreover, when a tip is broken or worn out the tip must be replaced. Current dental practice is that dental hand tools are sent to a professional service lab to sharpen or repair a tip, leading to inconvenience and increased cost to the office.

Dental instruments with replaceable tips are known to the art, but the performance of such tools has not been satisfactory. For example, U.S. Patent Application Publication No. 2012/0077148 to Luoto discloses a dental hand instrument comprising a handle, a detachable instrument head/tip, a fastening element for connecting the head/tip to the handle, and a tightening element that cooperates with the fastening element to secure the head/tip to the handle. One disadvantage of the Luoto device is that both right-handed and left-handed tips can be installed at either end of the instrument without the difference being readily observable to the casual observer. Thus, it is possible for an instrument to have two right-handed tips, or two left-handed tips, or one right-handed tip and one left-handed tip without the difference being noticeable by casual observation.

Another disadvantage of the Luoto device is that the connection between the handle and the detachable head/tip may not secure the tip in a manner effective to avoid unwanted movement of the tip relative to the handle. This causes the tip movement not to be as precise as is desired by many dental professionals.

A need currently exists for improved dental tools with tips that can be replaced at the dental office when a new or sharper tip is desired. The present invention addresses that need.

SUMMARY OF THE INVENTION

In one aspect of the present invention there is provided a dental instrument comprising:
a) a middle body;
b) a pair of removable instrument tips;
c) a pair of securing collets to assist in securing a tip to the middle body;
d) a pair of springs; and
e) a pair of removable end caps.

The middle body may comprise a shaft having a first end and a second end, with the first end terminating in a first middle body/instrument tip connection interface adapted to receive one of said instrument tips with a right-handed tip end only in a first orientation and adapted to receive one of said instrument tips with a left-handed tip end only in a second orientation differing from said first orientation, and with the second end terminating in a second middle body/instrument tip connection interface adapted to receive one of said instrument tips with a right-handed tip end only in a first orientation and adapted to receive one of said instrument tips with a left-handed tip end only in a second orientation differing from said first orientation.

Each of said removable instrument tips may comprise a middle body/instrument tip connection interface adapted to be removably connected to a corresponding middle body/instrument tip connection interface of either end of said middle body. Each of said removable instrument tips may also comprise a working tip end with either a right-handed or a left-handed orientation with respect to said middle body/instrument tip connection interface.

Each of said collets may comprise a generally cylindrical wall defining an inner bore sized to receive a portion of said middle body and a portion of one of said instrument tips, said wall having an outer surface sized to be received in the inner bore of one of said end caps.

Each of said removable end caps may comprise an inner bore sized to receive a portion of said middle body, a portion of one of said instrument tips, and one of said collets.

One of said instrument tips with a right-handed tip end may be releasably connected to said first middle body/instrument tip connection interface, and one of said instrument tips with a left-handed tip end may be releasably connected to said second middle body/instrument tip connection interface.

One of said collets may overlay the first middle body/instrument tip connection in a manner effective for securing an instrument tip to said middle body when the collet is held in place by said end cap, and one of said collets may overlay the second middle body/instrument tip connection in a manner effective for securing an instrument tip to said middle body when the collet is held in place by said end cap.

One of said springs may be positioned nearer the first end of said middle body to bias a collet toward the first end of the middle body, and one of said springs may be positioned nearer the second end of the middle body to bias a collet toward the second end of said middle body.

Each of said end caps may be releasably secured to the middle body in a manner effective to retain a collet and thereby to secure an instrument tip to said middle body.

In one embodiment each of the end caps has a proximal end and a distal end, and the device further includes an O-ring positioned around the middle body near the proximal end of the end cap in a manner effective to seal the proximal end of the end cap, and an O-ring positioned around the instrument tip near the distal end of the end cap in a manner effective to seal the distal end of the end cap.

In one embodiment each middle body/instrument tip connection interface of the middle body comprises a radial face and a longitudinal face, with the radial face and the longitudinal face being joined at an angle of less than 90°.

In one embodiment the middle body/instrument tip connection interface of both the middle body and the instrument tip comprises a radial face and a longitudinal face, and the longitudinal face of the instrument tip extends longitudinally for a distance greater than the distance that the longitudinal face of the middle body extends longitudinally.

In one embodiment the collet includes an indent having an indent diameter that is greater than the diameter of collet inner bore, and wherein said middle body includes a ridge having a ridge diameter that is greater than the collet inner bore diameter but less than the collet indent diameter.

In one embodiment the collet has a proximal end and a distal end, and longitudinal slots extending to the distal end and adapted to allow the distal end of the collet to deflect inward upon the application of an inward radial force upon the collet.

In one embodiment the middle body includes threads on its outer surface, wherein said end cap includes threads on its inner surface, and wherein the middle body threads cooperate with the end cap threads to allow said end cap to be screwed on to said middle body.

In one embodiment the collet wall comprises a distal end having a radially-extending end face, a longitudinally-extending portion, and an outer angled face connecting the end face to the outer surface.

In one embodiment the distal end of the collet additionally comprises an inner angled face, and the instrument tip comprises a retaining groove having a shoulder adapted to cooperate with the collet inner angled face to press said instrument tip end face against said middle body radial face in a manner effective to lock said instrument tip against said middle body upon tightening of said end cap.

In one embodiment the outer surface of the collet and the inner surface of the end cap are separated by a first gap, and the outer surface of the middle body retaining ring and the inner surface of the collet retaining groove are separated by a second gap, and the first gap is larger than the second gap.

BRIEF DESCRIPTION OF THE DRAWINGS

FIGS. 1A and 1B show one embodiment of the inventive dental instrument in partial (FIG. 1A) and full (FIG. 1B) longitudinal section.

DESCRIPTION OF THE PREFERRED EMBODIMENTS

Figure 2:
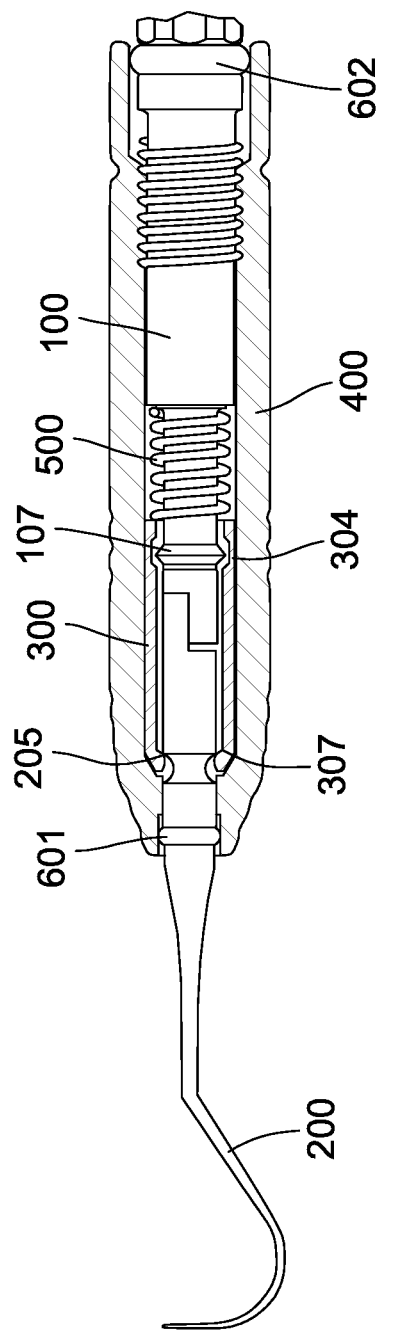
FIG. 2 is a longitudinal section view of one end of the inventive dental instrument according to one preferred embodiment.

For the purposes of promoting an understanding of the principles of the invention, reference will now be made to certain embodiments and specific language will be used to describe the same. It will nevertheless be understood that no limitation of the scope of the invention is thereby intended, with such alterations and modifications to the illustrated device being contemplated as would normally occur to one skilled in the art to which the invention relates.

As indicated above, one aspect of the present invention provides a dental tool with replaceable tips. The inventive dental instrument may comprise:
 a) a middle body;
 b) a pair of removable instrument tips;
 c) a pair of collets;
 d) a pair of springs; and
 e) a pair of removable end caps.

The inventive instrument is generally linear in shape as other, similar dental instruments are, with a working tip at each end. Since only one end of the tool is used at a time, it is convenient to refer to each end according to the orientation of that half while in use. Thus, for the purposes of this description, each half of the tool will be referred to as having "proximal" end portion and a "distal" end portion, with the proximal end portion of each half being closer to the user (i.e., closer to the middle of the tool) and the distal end portion of each half being farther from the user (i.e., closer to the end of the tool) while the relevant end of the tool is in use.

1. The Middle Body.

The middle body is the "frame" on which the other pieces are mounted, and preferably comprises a central shaft having a first end and a second end. To some extent the middle body can be thought of as the "handle" of the tool, although the majority of the middle body is typically covered by the end caps mounted on the middle body. In the preferred embodiments it is a combination of the end caps and the middle body that are actually gripped by the dentist/hygienist.

The first end of the middle body terminates in a first middle body/instrument tip connection interface adapted to receive a right-handed instrument tip only in a first orientation and adapted to receive a left-handed instrument tip only in a second orientation differing from said first orientation. Similarly, the second end of the middle body terminates in a second middle body/instrument tip connection interface adapted to receive a right-handed instrument tip only in a first orientation and adapted to receive a left-handed instrument tip only in a second orientation differing from said first orientation. The use of middle body/instrument tip connection interfaces that distinguish between right-handed tips and left-handed tips allows a user to determine by casual observation whether a desired right-handed/left-handed tip combination is installed on the device, or whether the device has two right-handed or two left-handed tips.

The middle body may include a central portion comprising flat surfaces for easy gripping when screwing the end caps onto the middle body. For example, the center portion of the middle body may have a hexagonal or octagonal shape when viewed in radial cross section. This allows a wrench or similar device to be used to grip the middle body when tightening or loosening an end cap.

Each half of the middle body has a proximal shaft portion and a distal shaft portion. As indicated above, each proximal shaft portion begins near the center of the middle body and extends outward toward one end of the tool. The distal shaft portion is the portion of the shaft nearer the end of the tool. The proximal shaft portion and the distal shaft portion may have the same diameter, or their diameters may be different. In the most preferred embodiment the proximal shaft portion has a diameter that is larger than the diameter of the distal shaft portion to allow the proximal shaft portion to terminate in a should that blocks a spring mounted to the distal shaft.

An indent or retaining groove for receiving an O-ring may be provided on each half of the middle body near its proximal end. The O-ring indent/retaining groove is used to hold an O-ring near the proximal end of an end cap to seal the end cap from dirt or other foreign matter.

Threads may be provided on each half of the middle body to allow end caps to be screwed to the middle body to secure the collets and end tips. Preferably the threads are provided near the proximal portion of each half of the shaft (i.e., near the center of the middle body). The middle body threads cooperate with the end cap threads to allow the end cap to be screwed on to the middle body.

The middle body/instrument tip connection interface portion of each end of the middle body preferably comprises a radially-extending surface, a longitudinally-extending surface, and an end surface which also extends radially. The radial surface and the end surface may have the shape of a semi-circle when the middle body shaft is round as shown in the Figures. In one embodiment the radial face and the longitudinal face are joined at an angle of less than 90°, and more preferably are joined at an angle of between 85° and 89°, most preferably between 86° and 88°. The angle between the longitudinal face and the end face is preferably about 90°.

The middle body is preferably made of metal or a composite material that is strong and rigid and allows cleaning using standard dental office cleaning technology.

2. The Removable Instrument Tips.

The inventive dental instrument preferably has two instrument tips—one tip at each end. Each of those removable instrument tips may comprise a working instrument end with either a right-handed or a left-handed orientation with respect to said middle body/instrument tip connection interface. As is known to the art, a right-handed tip differs from a left-handed tip by the location and/or orientation of the working edge(s) of the tip. To facilitate use by dental professionals using traditional techniques, it is often desirable for a hand instrument to have a right-handed tip at one end and a left-handed tip at the other end.

As with the middle body, each instrument tip includes a middle body/instrument tip connection interface portion. In the most preferred embodiments the middle body/instrument tip connection interface portion of each instrument tip preferably comprises a radially-extending surface, a longitudinally-extending surface, and an end surface which also extends radially. As with the middle body, the radial surface and the end surface of the middle body/instrument tip connection interface portion of each instrument tip may have the shape of a semi-circle when the middle body shaft is round as shown in the Figures. In one embodiment the longitudinal face and the end face are joined at an angle that is equal to the angle of the radial face and the longitudinal face of the middle body/instrument tip connection interface portion of the corresponding middle body. That allows the end face of the instrument tip to fit securely against the radial face of the middle body when the instrument tip is locked into place by an end cap.

An indent with a shoulder adapted to cooperate with a collet end may be provided in the proximal shaft of the instrument tip. The instrument tip collet indent cooperates with one end of a collet to lock the instrument tip into position when the end cap is screwed tight.

An O-ring indent/retaining groove may be provided on the instrument tip shaft. When positioned thereon an O-ring seals the distal end of the end cap from dirt or other foreign matter.

The instrument tips are preferably made of metal or a composite material that is strong and rigid and allows cleaning using standard dental office cleaning technology.

3. The Middle Body/Instrument Tip Connection Interface.

As indicated above, each half of the middle body has a middle body/instrument tip connection interface portion, and each instrument tip also has a middle body/instrument tip connection interface portion. The middle body/instrument tip connection interface portion of an instrument tip cooperates with the middle body/instrument tip connection interface portion of one half of the middle body to allow an instrument tip to be securely connected to the middle body in a manner that allows a user to see by casual observation whether a right-handed tip and a left-handed tip are installed on the device. Similarly, the middle body/instrument tip connection interface allows a user to see by casual observation whether two right-handed tips or two left-handed tips are installed on the device.

As described above, in the most preferred embodiments each middle body/instrument tip connection interface portion comprises a radial face, a longitudinal face, and an end face. The two longitudinal faces contact each other when a tip is installed, and the end face of an instrument tip presses against the radial face of the middle body. The end face of the middle body is preferably separated from the radial face of the instrument tip by a small gap. The gap may be provided by having the longitudinal face of the instrument tip extend longitudinally for a distance greater than the distance that the longitudinal face of the middle body extends.

The two pieces of the middle body/instrument tip connection interface are preferably held together by a securing collet as described below. The securing collet pushes the slightly-angled end face of the instrument tip against the correspondingly-angled radial face of the middle body, with the two longitudinal faces sliding against each other. This locks the end of the instrument tip against the middle body in a manner that prevents the tip from twisting or turning or otherwise moving with respect to the middle body.

A right-handed instrument tip may be releasably connected to one middle body/instrument tip connection interface, and a left-handed instrument tip may be releasably connected to the opposite middle body/instrument tip connection interface. If the middle body/instrument tip connection interfaces are oriented as shown in the Figures, it will be apparent to an observer using casual observation that both right-handed and left-handed tips are installed. It will also be apparent to an observer using casual observation that both right-handed and left-handed tips are installed.

4. The Securing Collet.

In one embodiment the inventive device additionally includes a securing collet, although the collet may not be required if other means are used to hold the instrument tip securely against the middle body. When used, the collet preferably has a distal end that contracts and pushes against the instrument tip in a manner effective to lock the tip to the middle body.

In one embodiment the collet includes an indent having an indent diameter that is greater than the diameter of collet inner bore. This indent aligns with a ridge on the middle body to limit the movement of the collet with respect to the middle body. The middle body ridge has a diameter that is greater than the collet inner bore diameter but less than the collet indent diameter, so that the ridge moves but is retained within the collet indent space.

In one embodiment the collet has a proximal end and a distal end, and longitudinal slots extending to the distal end and adapted to allow the distal end of the collet to deflect inward upon the application of an inward radial force upon the collet.

The collets preferably comprise a generally cylindrical wall defining an inner bore sized to receive a portion of said middle body and a portion of one of said instrument tips, said wall having an outer surface sized to be received in the inner bore of one of said end caps.

One of the collets preferably overlays the first middle body/instrument tip connection in a manner effective for securing an instrument tip to said middle body when the collet is held in place by said end cap, and another collet preferably overlays the second middle body/instrument tip connection in a manner effective for securing an instrument tip to said middle body when the collet is held in place by said end cap.

In one embodiment the collet wall comprises a distal end having a radially-extending end face, a longitudinally-extending portion, and an outer angled face connecting the end face to the outer surface. The distal end of the collet may additionally comprise an inner angled face that cooperates with an instrument tip retaining groove shoulder to press the instrument tip end face against the middle body radial face in a manner effective to lock said instrument tip against said middle body upon tightening of said end cap.

In one embodiment the outer surface of the collet and the inner surface of the end cap are separated by a first gap, and the outer surface of the middle body retaining ring and the inner surface of the collet retaining groove are separated by a second gap, and the first gap is larger than the second gap.

The collets are preferably made of metal or a composite material that is strong and rigid and allows cleaning using standard dental office cleaning technology.

5. The End Caps.

The inventive device preferably includes removable end caps on each end to secure the instrument tip in place against the middle body. In the preferred embodiment each removable end cap comprises an inner bore sized to receive a portion of the middle body, a portion of one of the instrument tips, and one of the securing collets.

Each of said end caps may be releasably secured to the middle body in a manner effective to retain a collet and thereby to secure an instrument tip to said middle body. In one embodiment the end cap includes threads on its inner surface, with the end cap threads being adapted to cooperate with corresponding threads on the middle body to allow each end cap to be screwed on to said middle body.

In one embodiment each of the end caps has a proximal end and a distal end. The distal end preferably includes an angled face and a radial face, with the angled face being effective for pushing the distal outer angled face of a collet inward to tighten the collet. The distal end additionally preferably comprises a radial face to push against an end face of a collet to move the collet rearward (toward the proximal end of one half of the device) after the angled face has sufficiently tightened the collet.

The end caps are preferably made of metal or a composite material that is strong and rigid and allows cleaning using standard dental office cleaning technology.

6. The Springs.

The inventive device preferably includes a spring or other means for biasing the collet toward the nearest distal end of the device. In the most preferred embodiments there are two springs, with one spring being positioned nearer the first end of said middle body to bias a collet toward the first end of the middle body, and another spring being positioned nearer the second end of the middle body to bias a collet toward the second end of said middle body. The springs are preferably coil springs sized to fit around the distal shank portion of the middle body between the middle body spring shoulder and the middle body distal ridge. The springs are preferably selected to provide a biasing force effective to bias the collet toward the distal end without preventing the collet from being pushed toward the proximal end when the end cap is screwed by a hygienist hand onto the middle body.

7. Assembly of the Device and Changing a Tip of the Device.

The device may be provided to the dental professional as a body portion and removable tips. The body portion typically includes a middle body with collets at each end, springs biasing the collets outward, and the end caps loosely screwed onto the body. The distal collet ends are relatively open to receive an instrument tip.

To assemble the device an instrument tip is pushed into the opening of each end cap so that the proximal end of the instrument tip aligns with and begins to lock into the middle body/instrument tip interface as illustrated in the drawings. The end caps are then screwed to tighten the cap, thereby moving the end cap longitudinally toward the center of the middle body. As the end cap advances over the middle body, the angled inner face of the end cap contacts the outer angled face of the collet, causing the collet to compress inward. As the end cap further advances over the middle body, the longitudinal face of the collet contacts the collet end face, stopping further compressive movement of the collet and causing the collet to move rearwards (i.e., toward the middle of the device) until the collet inner angled face presses against the instrument tip retaining groove shoulder. As the end cap is finally tightened, the collet inner angled face presses firmly against the instrument tip shoulder, pressing the instrument tip firmly into the middle body/instrument tip connection interface and locking the instrument tip into place. The spring is compressed during this action.

Similarly, to replace a tip the appropriate end cap is unscrewed until the collet moves (by the decompressing movement of the spring) to its open position and the old tip is removed. A new tip in inserted and the end cap is screwed tight to press the collet against the tip shoulder and to press the tip against the middle body—thereby locking the tip against the middle body.

8. Discussion of the Drawings.

Referring now to the drawings, FIGS. 1A and 1B show one preferred embodiment of the inventive device. The instrument comprises a middle body 100, a pair of instrument tips 200, a pair of collets 300, a pair of end caps 400, and a pair of springs 500. In Figure 1A the end cap has not been tightened fully and the collet is therefore not in its locked position. In FIG. 1B the end cap has been tightened fully and the collet is in its locked position.

FIG. 2 shows another view of one end of the inventive device according to one preferred embodiment. Middle body 100, an instrument tip 200, a collet 300, an end cap 400, and a spring 500 are illustrated. Middle body distal ridge 107 is contained within collet indent/retaining ring 304, and collet inner angled face 307 presses against instrument tip retaining groove shoulder 205 to lock the instrument tip in place. O-rings 601 and 602 protect the distal and proximal ends of the device.

Figure 3:
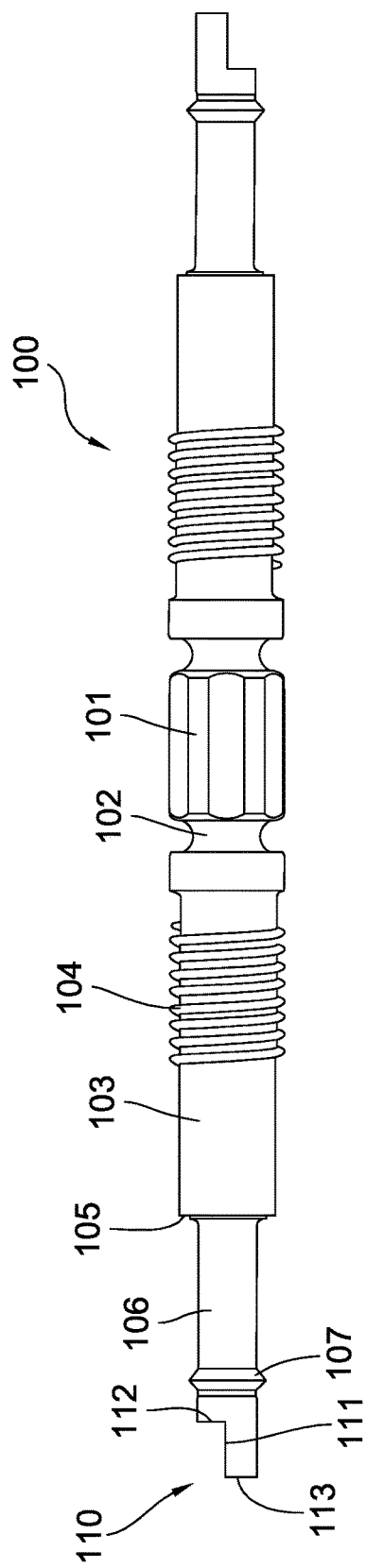
FIG. 3 shows a middle body of the inventive dental instrument according to one preferred embodiment.

FIG. 3 shows a middle body of the inventive dental instrument according to one preferred embodiment. Middle body central portion 101 provides flat surfaces for easy gripping when screwing the end caps onto the middle body. Middle body O-ring retaining grooves 102 for receiving an O-ring are provided on each half of the middle body near its proximal end to hold an O-ring to seal the end cap from dirt or other foreign matter. Middle body proximal shaft portion 103 includes threads 104 to allow end caps to be screwed to the middle body to secure the collets and end tips. Middle body proximal shaft portion 103 terminates in a spring shoulder 105 provided to butt against a spring that overlays distal portion 106 and to keep the spring from moving over proximal shaft portion 103. Distal end portion 106 includes ridge 107 and terminates in a middle body/instrument tip connection interface portion that allows an instrument tip to be securely connected to the middle body in a manner that allows a user to see by casual observation whether a right-handed tip and a left-handed tip are installed on the device. Middle body/instrument tip connection interface 110 includes longitudinal face 111, radial face 112, and end face 113. Longitudinal face 111 is joins radial face 112 at a slight angle which is preferably between about 85° and 89°, and more preferably between about 87° and 89°.

Figure 4:
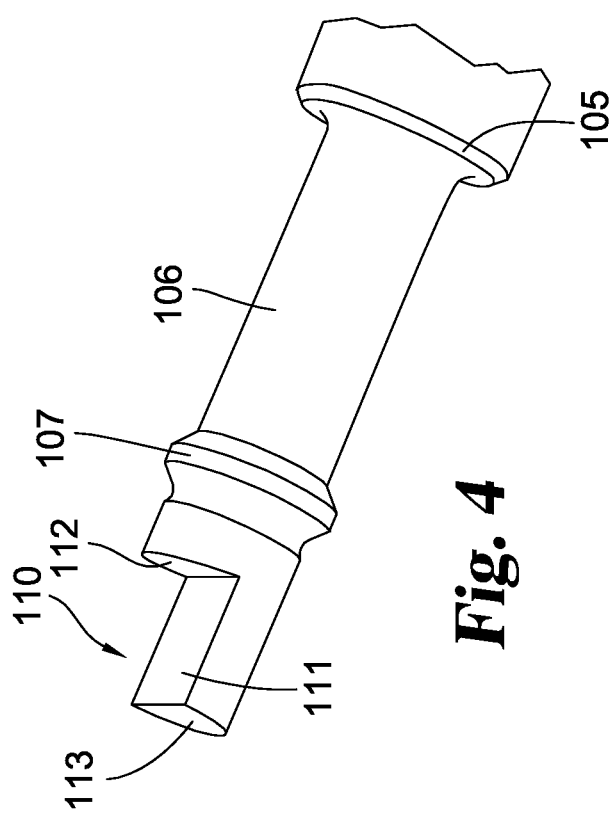
FIG. 4 is a perspective view of one end of a middle body of the inventive dental instrument, according to one preferred embodiment.

FIG. 4 is a perspective view of one end of a middle body of the inventive dental instrument, according to one preferred embodiment. Spring shoulder 105 is effective for blocking a spring from sliding over proximal shaft portion 103. Distal end portion 106 includes distal ridge 107 and middle body/instrument tip connection interface 110. Middle body/instrument tip connection interface 110 includes longitudinal face 111, radial face 112, and end face 113.

Figure 5:
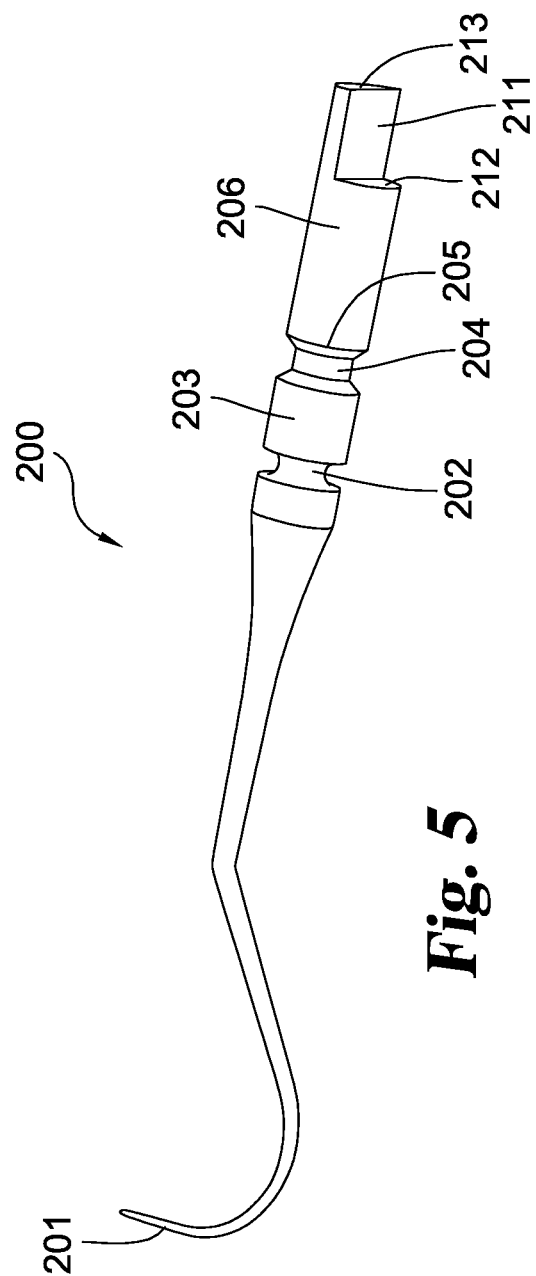
FIG. 5 is a perspective view of one embodiment of an instrument tip of the inventive dental instrument.

FIG. 5 is a perspective view of one embodiment of an instrument tip of the inventive dental instrument. Instrument tip 200 includes a working tip end 201, a distal shaft portion 203, and a proximal shaft portion 206. An O-ring retaining groove 202 is provided in distal shaft portion 203 to retain an O-ring to seal the tip end of the device from contamination. Collet locking groove 204 is provided adjacent proximal shaft portion 204, with locking shoulder 205 being provided to cooperate with a collet to press the instrument tip against the middle body, thus locking the tip in place. Middle body/instrument tip connection interface 210 includes a longitudinal face 211 and a radial face 212 and an end face 213. End face 213 is joined to longitudinal face 222 at an angle corresponding to the angle formed by the longitudinal and radial faces of the middle body, thus allowing the instrument tip end to lock into the middle body/instrument tip connection interface to lock the instrument tip into place.

Figure 6:
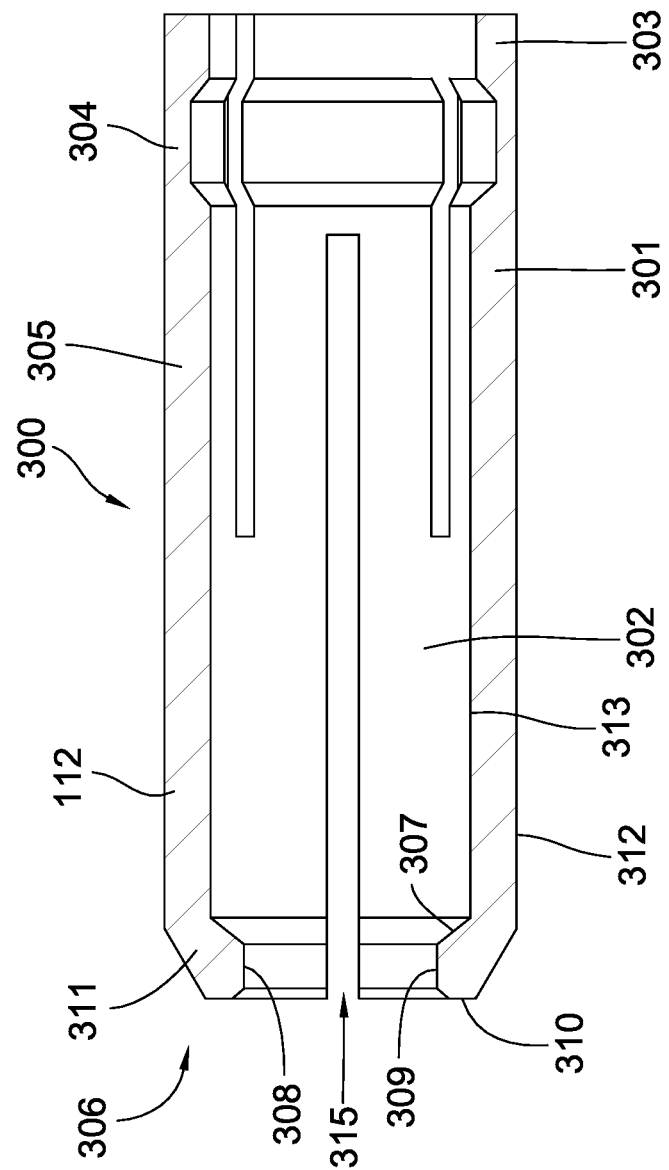
FIG. 6 is a longitudinal section view of one embodiment of a securing collet of the inventive dental instrument.

FIG. 6 is a longitudinal section view of one embodiment of a securing collet of the inventive dental instrument. Collet 300 includes collet wall 301 defining collet bore 302. Collet wall 301 includes a proximal end portion 303 and a collet indent/retaining ring 304 adapted to receive middle body distal ridge 107 to properly position the collet on middle body 100. The main bore wall 305 includes proximal slots 315 and distal slots 317 that allow the collet to compress inwardly and/or expand outwardly as needed. Collet distal end 306 includes a distal inner angled face 307, a distal longitudinal face 308, a distal trailing face 309, a distal end face 310, and a distal outer angled face 311. Moreover, collet wall 301 includes an inner surface 312 and an outer surface 313.

Figure 7:
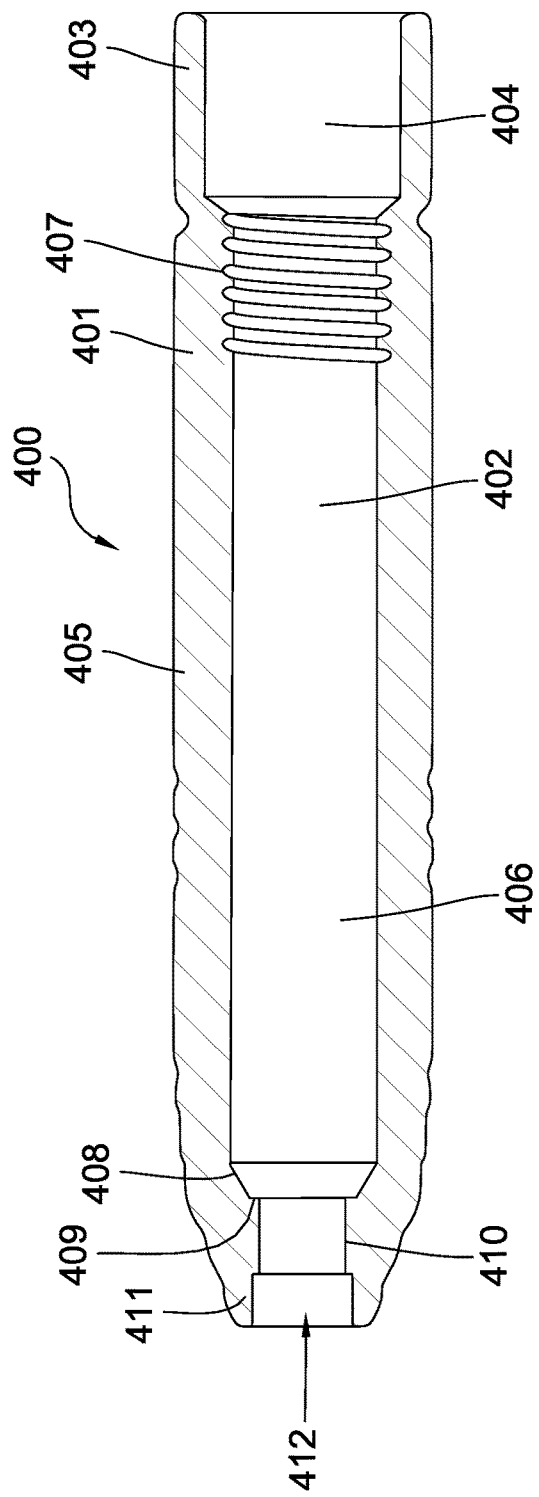
FIG. 7 is a longitudinal section view of one embodiment of an end cap of the inventive dental instrument.

FIG. 7 is a longitudinal section view of one embodiment of an end cap of the inventive dental instrument. End cap 400 includes a wall 401 defining a bore 402. Wall 401 includes a proximal portion 403 defining a proximal bore portion 404, and a central portion 405 defining a central bore portion 406. Central bore portion 406 preferably has a diameter that is smaller than the diameter of proximal bore portion 404. Threads 407, that cooperate with corresponding middle body threads 104, are preferably provided at the transition between proximal bore portion 404 and central bore portion 406. Proximal bore portion 404 is preferably sized to provide a slight interference fit over O-ring 602, thus slightly compressing O-ring 602 to allow it to snuggly seal proximal bore 404.

End cap wall 401 has an inner surface that includes, near its distal end portion, an angled leading face 408 and a radial face 409. As end cap is screwed against collet 300, leading face 408 will contact distal outer angled face 311 and will compress collet distal end 306 inward. When end cap 400 has been screwed a distance sufficient for radial face 409 to contact collet end wall 310, further movement of end cap 400 will push the collet backward to its locked position.

End cap bore 402 may terminate in a distal end portion 411 that includes a distal bore 412 with a diameter sized to cooperate with O-ring 601 to provide a slight interference fit over O-ring 601, thus slightly compressing O-ring 601 to allow it to snuggly seal distal bore 412. A transition portion 410 may be provided between radial face 409 and distal end portion 411.

Figure 8A:
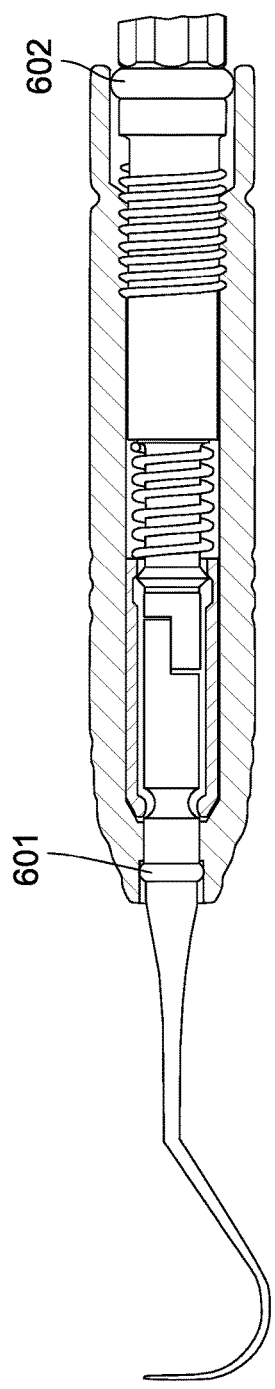
FIGS. 8A and 8B are longitudinal section views of one end of the inventive dental instrument, according to one preferred embodiment, showing the collet in pre-locked (FIG. 8A) and locked (FIG. 8B) positions.
Figure 8B:
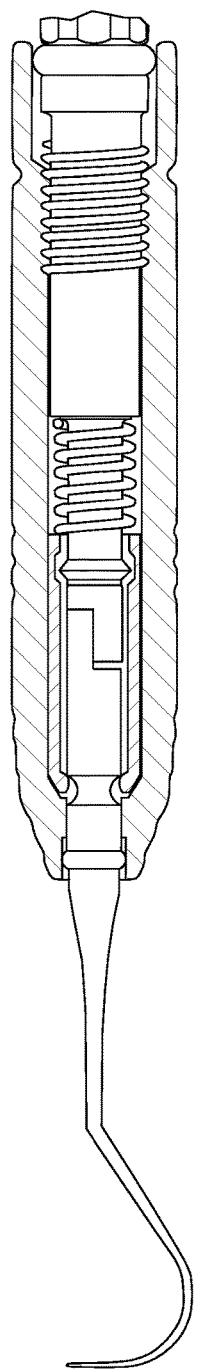

FIGS. 8A and 8B are longitudinal section views of one end of the inventive dental instrument, according to one preferred embodiment, showing the collet in pre-locked (FIG. 8A) and locked (FIG. 8B) positions. In the pre-locked position illustrated in FIG. 8A, end cap leading face 408 is contacting collet outer angled face 311 and is just beginning to compress the collet inward. End cap radial face 409 has not yet contacted collet end face 310 and has therefore not yet begun to push collet inner angled face 307 against instrument tip locking shoulder 205.

In the locked position illustrated in FIG. 8B, end cap radial face 409 has contacted collet end face 310 and has pushed collet inner angled face 307 against instrument tip locking shoulder 205. Instrument tip longitudinal face 211 has moved along middle body longitudinal face 111, and instrument tip radial face 212 is locked against middle body radial face 112. The angle of instrument tip radial face 212 and middle body radial face 112 cooperates with longitudinal faces 111 and 211 to prevent the instrument tip from turning with respect to the middle body. A slight gap remains between middle body end face 112 and instrument tip radial face 212.

Figure 9:
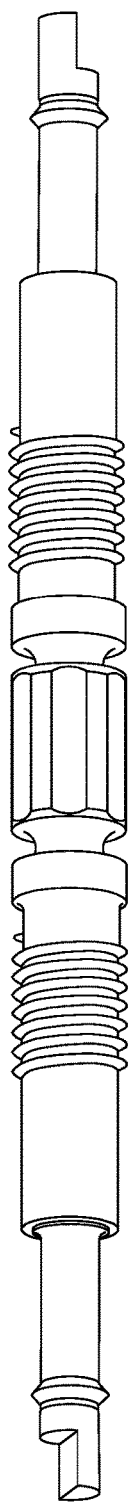
FIG. 9 shows a middle body of the inventive dental instrument according to one preferred embodiment.

FIG. 9 shows further aspects of middle body 100 previously illustrated and described.

Figure 10:
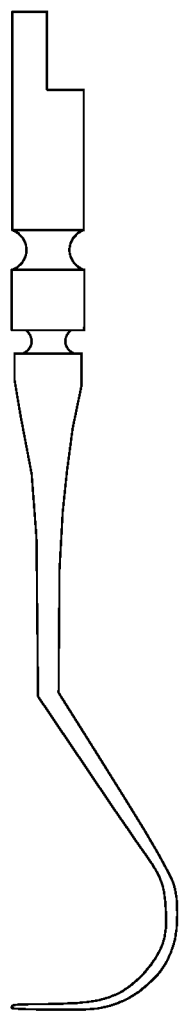
FIG. 10 shows an instrument tip of the inventive dental instrument according to one preferred embodiment.

FIG. 10 shows further aspects of instrument tip 200 previously illustrated and described.

Figure 11:
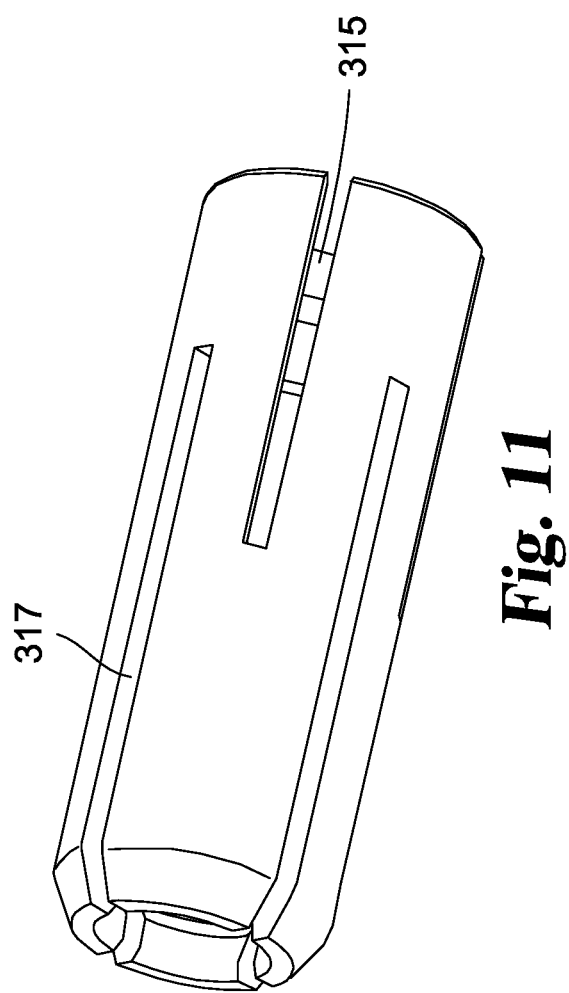
FIG. 11 shows a collet of the inventive dental instrument according to one preferred embodiment.

FIG. 11 shows further aspects of collet 300 previously illustrated and described. Proximal slots 315 and distal slots 317 can be seen.

Figure 12:
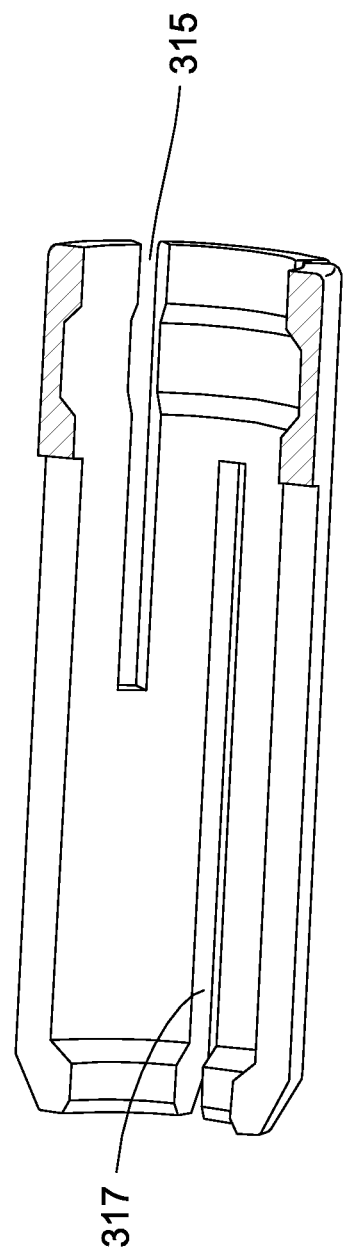
FIG. 12 shows a partial section view of a collet of the inventive dental instrument according to one preferred embodiment.

FIG. 12 shows further aspects of collet 300 previously illustrated and described. Proximal slots 315 and distal slots 317 can be seen.

Figure 13:
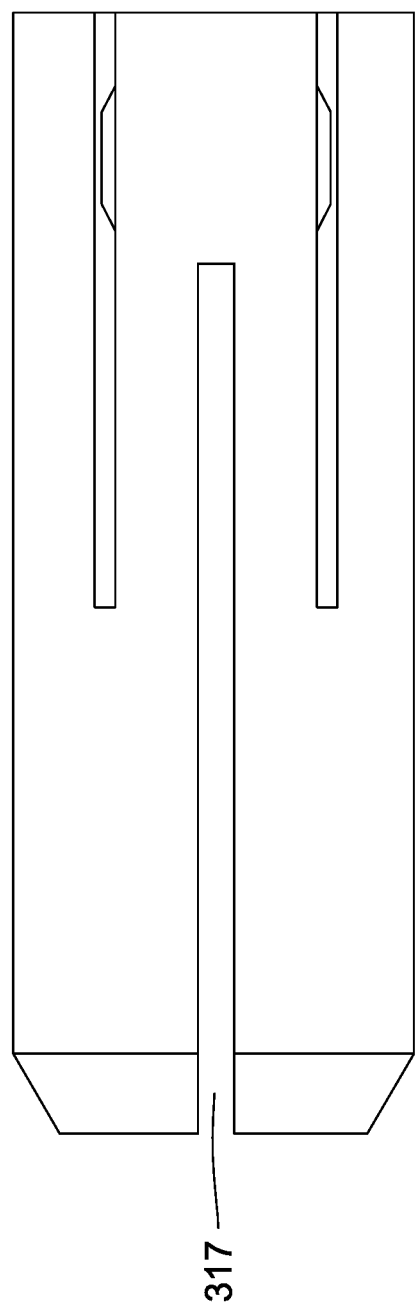
FIG. 13 shows another view of a collet of the inventive dental instrument according to one preferred embodiment.

FIG. 13 shows further aspects of collet 300 previously illustrated and described. Distal slots 317 can be seen.

Figure 14:
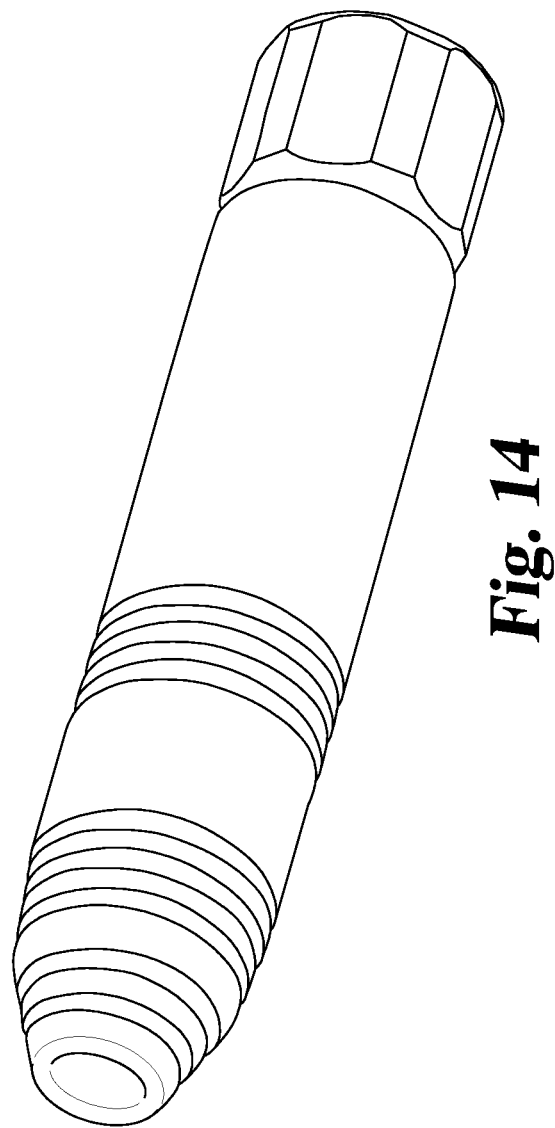
FIG. 14 shows an end cap of the inventive dental instrument according to one preferred embodiment.

FIG. 14 shows further aspects of end cap 400 previously illustrated and described.

Figure 15:
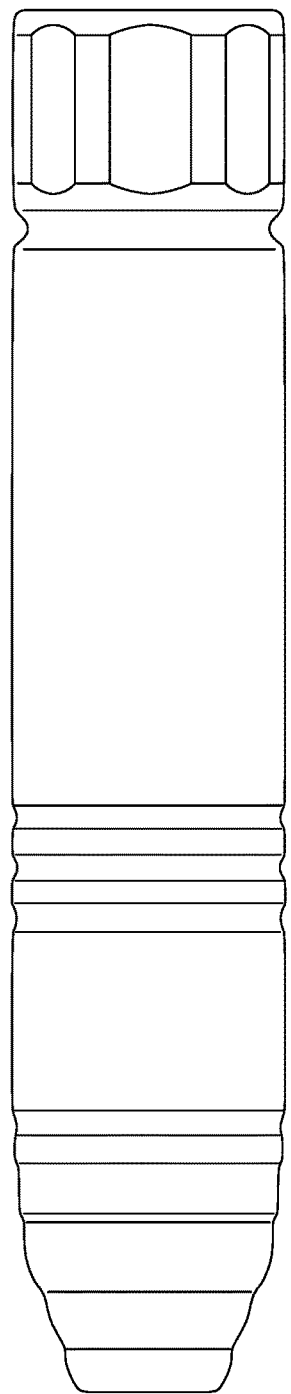
FIG. 15 shows another view of an end cap of the inventive dental instrument according to one preferred embodiment.

FIG. 15 shows further aspects of end cap 400 previously illustrated and described.

Figure 16:
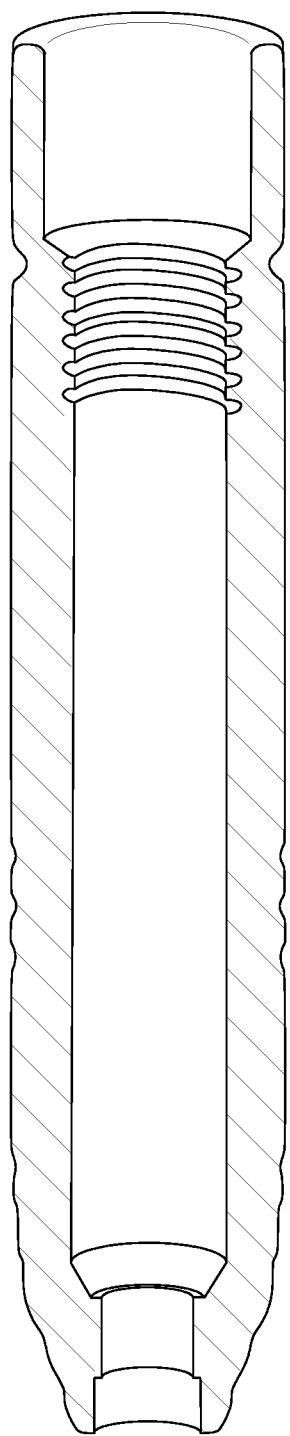
FIG. 16 shows a partial section view of an end cap of the inventive dental instrument according to one preferred embodiment.

FIG. 16 shows further aspects of end cap 400 previously illustrated and described.

Figure 17A:
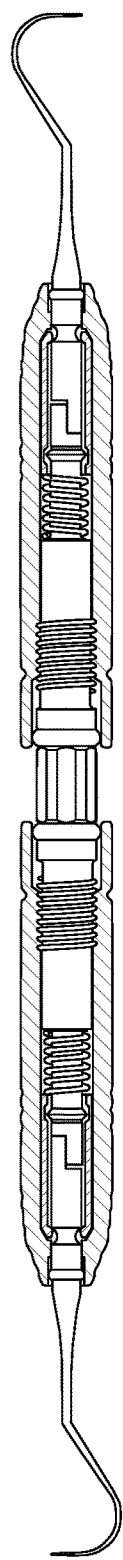
FIG. 17A shows a longitudinal section view of one embodiment of the inventive dental instrument with right-handed and left-handed tips installed.

FIG. 17A shows a longitudinal section view of one embodiment of the inventive dental instrument with right-handed and left-handed tips installed. In the illustrated embodiment a right-handed tip has its tip end facing in a specific direction (for example, toward the longitudinal face and away from the radial face) with respect to the longitudinal and radial faces of the instrument tip, while a left-handed instrument tip has its tip end facing in the opposite direction (for example, toward the radial face and away from the longitudinal face) with respect to the longitudinal and radial faces of the instrument tip. Since the two instrument tips have the same middle body/instrument tip interface, and since the two instrument tips face in opposite directions, it can be seen from casual observation that both a right-handed and a left-handed instrument tip are installed in the device.

Figure 17B:
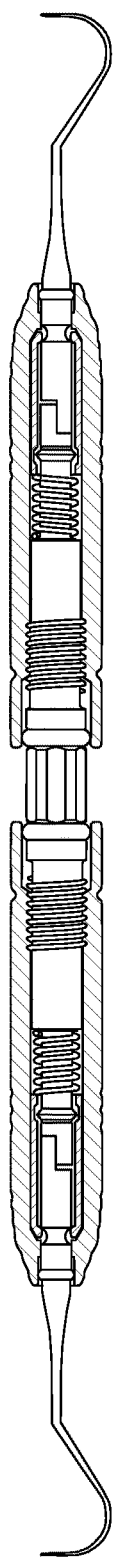
FIG. 17B shows a longitudinal section view of one embodiment of the inventive dental instrument with two right-handed or two left-handed tips installed.

FIG. 17B shows a longitudinal section view of one embodiment of the inventive dental instrument with two right-handed or two left-handed tips installed. Since the two instrument tips have the same middle body/instrument tip interface, and since the two instrument tips face in the same direction, it can be seen from casual observation that two right-handed tips or two left-handed tips are installed in the device.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, it is to be appreciated that the present invention may comprise or consist essentially of any or all of the illustrated or described devices. For example, the present invention includes devices comprising each of the embodiments illustrated in FIGS. 1 through 17, and the present invention includes devices consisting essentially of any of the embodiments illustrated in FIGS. 1 through 17. Additionally, any or all of the features and/or embodiments disclosed herein may be combined with any or all of the other features and/or embodiments disclosed herein to provide a device that comprises or consists essentially of such features.

The invention claimed is:

1. A dental instrument device, comprising:
 a) a middle body;
 b) a pair of removable instrument tips;
 c) a pair of collets;
 d) a pair of springs; and
 e) a pair of removable end caps;
 wherein said middle body comprises a shaft having a first end and a second end and defining a longitudinal axis therebetween, with the first end terminating in a first middle body/instrument tip connection interface comprising an instrument tip contacting surface having a radial face and a longitudinal face and adapted to receive one of said removable instrument tips with a right-handed tip end only in a first orientation and adapted to receive one of said removable instrument tips with a left-handed tip end only in a second orientation differing from said first orientation, and with the second end terminating in a second middle body/instrument tip connection interface adapted to receive one of said removable instrument tips with a right-handed tip end only in said first orientation and adapted to receive one of said removable instrument tips with a left-handed tip end only in said second orientation differing from said first orientation;
 wherein each one of said pair of removable instrument tips comprises a middle body/instrument tip connection interface comprising a middle body contacting surface having a radial face and a longitudinal face, and a working tip end with either a right-handed or a left-handed orientation with respect to said middle body/instrument tip connection interface;
 wherein each one of said pair of collets comprises a generally cylindrical wall defining an inner bore sized to receive a portion of said middle body and a portion of one of said instrument tips, said wall having an outer surface sized to be received in an inner bore of one of said end caps;
 wherein each one of said pair of removable end caps comprises an inner bore sized to receive a portion of said middle body, a portion of one of said instrument tips, and one of said collets;
 wherein one of said removable instrument tips with a right-handed tip end is releasably connected to said first middle body/instrument tip connection interface, and one of said removable instrument tips with a left-handed tip end is releasably connected to said second middle body/instrument tip connection interface;
 wherein one of said pair of collets overlays said first middle body/instrument tip connection in a manner effective for securing one of said removable instrument tips to said middle body when the collet is held in place by said end cap, and one of said pair of collets overlays said second middle body/instrument tip connection in a manner effective for securing one of said removable instrument tips to said middle body when the collet is held in place by said end cap;
 wherein one of said pair of springs is positioned nearer the first end of said middle body and biases one of said pair of collets along the longitudinal axis away from the second end of said middle body, and one of said pair of springs is positioned nearer the second end of said middle body and biases one of said pair of collets along the longitudinal axis away from the first end of said middle body; and
 wherein each one of said pair of end caps is releasably secured to said middle body in a manner effective to retain one of said pair of collets and thereby to secure one of said removable instrument tips to said middle body.

2. A dental instrument according to claim 1 wherein each of said removable end caps has a proximal end and a distal end, and wherein said device further includes a first O-ring positioned around said middle body near the proximal end of one of said removable end caps in a manner effective to seal the proximal end of that end cap, and wherein the device further includes a second O-ring positioned around one of said removable instrument tips near the distal end of one of said removable end caps in a manner effective to seal the distal end of that end cap.

3. A dental instrument according to claim 1 wherein the radial face and the longitudinal face of the middle body/ instrument tip connection interface of said middle body are joined at an angle of less than 90°.

4. A dental instrument according to claim 1 wherein the longitudinal face of the middle body/instrument tip connection interface of each instrument tip extends longitudinally for a distance greater than the longitudinal distance that the longitudinal face of the middle body/instrument tip connection interface of said middle body extends.

5. A dental instrument according to claim 1 wherein each one of said collet's includes an indent having an indent diameter that is greater than the diameter of that collet's inner bore, and wherein said middle body includes a ridge having a ridge diameter that is greater than the collet inner bore diameter but less than the collet indent diameter.

6. A dental instrument according to claim 1 wherein each one of said collets has a proximal end portion and a distal end portion, wherein the distal end portion includes one or more longitudinal slots extending to the distal end and adapted to allow the distal end of the collet to deflect inward upon the application of an inward radial force upon the collet, and wherein the proximal end portion includes one or more longitudinal slots extending to the proximal end to allow the proximal end of the collet to expand or compress.

7. A dental instrument according to claim 1 wherein said middle body includes threads on its outer surface, wherein said end cap includes threads on its inner surface, and wherein the middle body threads cooperate with the end cap threads to allow said end cap to be screwed on to said middle body.

8. A dental instrument according to claim 1 wherein said collet wall comprises a distal end having a radially-extending end face, a longitudinally-extending portion, and an outer angled face connecting the end face to the outer surface.

9. A dental instrument according to claim 1 wherein said collet distal end additionally comprises an inner angled face, and wherein said instrument tip comprises a retaining groove having a shoulder adapted to cooperate with the collet inner angled face to press said instrument tip end face against said middle body radial face in a manner effective to lock said instrument tip against said middle body upon tightening of said end cap.

10. A dental instrument according to claim 1 wherein the outer surface of the collet and the inner surface of the end cap are separated by a first gap, and the outer surface of the middle body retaining ring and the inner surface of the collet retaining groove are separated by a second gap, and said first gap is larger than said second gap.

11. A dental instrument device, comprising:
a) a middle body;
b) a removable instrument tip,;
c) a collet;
d) a removable end cap having an inner bore;
wherein said middle body comprises a shaft having a first end terminating in a first middle body/instrument tip connection interface adapted to receive said removable instrument tip;
wherein said removable instrument tip comprises a working tip end and a middle body/instrument tip connection interface adapted to be removably connected to the middle body/instrument tip connection interface of said middle body;
wherein said collet comprises a generally cylindrical wall defining an inner bore sized to receive a portion of said middle body and a portion of said removable instrument tip, said wall having an outer surface sized to be received in the inner bore of said removable end cap;
wherein said removable end cap comprises an inner bore sized to receive a portion of said middle body, a portion of said instrument tip, and said collet;
wherein said removable instrument tip is releasably connected to said first middle body/instrument tip connection interface by longitudinal movement of said removable cap end in a manner effective to longitudinally move said collet in a manner effective to radially contract one end of said collet and thereby to lock said instrument tip against said middle body;
wherein said instrument tip includes an instrument tip shoulder; wherein said collet includes a distal end having an inner angled face, an outer angled face, and an end face; wherein said end cap includes an inner angled face and an inner longitudinal face; and wherein said instrument tip is locked against said middle body by: a) the longitudinal movement of said end cap end in a manner effective to cause the end cap inner angled face to push against the collet outer angled face, thereby causing said collet to contract radially inward until the end cap longitudinal face contacts the collet end face, and subsequently by: b) the longitudinal movement of the end cap in a manner effective to cause the end cap inner longitudinal face to contact the collet end face and to push said collet against said instrument tip shoulder in a manner effective to lock said instrument tip against said middle body.

12. A kit for providing a dental instrument device, comprising:
a) a middle body having a first end and a second end and defining a longitudinal axis therebetween;
b) an instrument tip with a right-hand orientation;
c) an instrument tip with a left-hand orientation;
c) two collets;
d) two springs; and
e) two removable end caps;
wherein said middle body includes a first threaded portion adapted to engage a threaded portion of a first one of said end caps to cause said first end cap to advance along the longitudinal axis of the device upon rotation of the end cap, and a second threaded portion adapted to engage a threaded portion of a second one of said end caps to cause said second end cap to advance along the longitudinal axis of the middle body upon rotation of the end cap;
wherein the first end of said middle body terminates in instrument tip contacting surfaces comprising a radial face and a longitudinal face, with the radial face and the longitudinal face being joined at an angle of less than 90°; and
wherein the second end of said middle body terminates in instrument tip contacting surfaces comprising a radial face and a longitudinal face, with the radial face and the longitudinal face being joined at an angle of less than 90°;
wherein each of said removable instrument tips comprises middle body contacting surfaces comprising a radial face and a longitudinal face;
wherein each of said removable instrument tips comprises a shoulder portion engageable with an inner angled face of each of said collets;
wherein each of said collets comprises a generally cylindrical wall defining an inner bore sized to receive a portion of said middle body and a portion of one of said instrument tips, and an inner angled face adapted to engage a shoulder of said instrument tips;

wherein each of said end caps includes a threaded portion adapted to engage one of said first or second threaded portions of said middle body to cause the end cap to advance along the longitudinal axis of the middle body upon rotation of the end cap;

wherein one of said springs is positioned nearer the first end of said middle body and is effective to bias a collet along the longitudinal axis away from the second end of said middle body, and one of said springs is positioned nearer the second end of said middle body and is effective to bias a collet along the longitudinal axis away from the first end of said middle body;

wherein the middle body, collets, end caps, and instrument tips are adapted such that when the instrument tip contacting surfaces of the middle body are adjacent the middle body contacting surfaces of an instrument tip, and a collet overlays the middle body contacting surfaces and the instrument tip contacting surfaces, and an end cap overlays the collet, the rotation of the end cap to engage the threads of the middle body causes the end cap to move longitudinally in a manner effective to push the inner angled face of the collet to engage the shoulder portion of the instrument tip, and thereby to push the middle body contacting surfaces of the instrument tip into locking contact with the instrument tip contacting surfaces of the middle body.

* * * * *